(12) United States Patent
Fosaaen

(10) Patent No.: US 10,138,782 B2
(45) Date of Patent: *Nov. 27, 2018

(54) MICROCHIP OXYGEN SENSOR FOR CONTROL OF INTERNAL COMBUSTION ENGINES OR OTHER COMBUSTION PROCESSES

(71) Applicant: Kerdea Technologies, Inc., Greenville, NC (US)

(72) Inventor: Ken Ervin Fosaaen, Winterville, NC (US)

(73) Assignee: KERDEA TECHNOLOGIES, INC., Greenville, NC (US)

( * ) Notice: Subject to any disclaimer, the term of this patent is extended or adjusted under 35 U.S.C. 154(b) by 231 days.

This patent is subject to a terminal disclaimer.

(21) Appl. No.: 15/176,383

(22) Filed: Jun. 8, 2016

(65) Prior Publication Data

US 2017/0058741 A1    Mar. 2, 2017

Related U.S. Application Data

(63) Continuation of application No. 14/073,182, filed on Nov. 6, 2013, which is a continuation of application
(Continued)

(51) Int. Cl.
*F01N 11/00* (2006.01)
*F01N 3/20* (2006.01)
(Continued)

(52) U.S. Cl.
CPC .......... *F01N 3/2026* (2013.01); *F01N 11/002* (2013.01); *F02D 41/042* (2013.01);
(Continued)

(58) Field of Classification Search
CPC ............... F02D 41/1455; F02D 41/123; F02D 41/1441; F02D 41/1456; F02D 41/1495;
(Continued)

(56) References Cited

U.S. PATENT DOCUMENTS

| 4,245,314 A | 1/1981 | Henrich et al. |
| 4,263,652 A | 4/1981 | Henrich |

(Continued)

FOREIGN PATENT DOCUMENTS

| CN | 101825032 A | 9/2010 |
| JP | 0743342 A | 2/1995 |

(Continued)

*Primary Examiner* — Randy Gibson
*Assistant Examiner* — Gedeon M Kidanu
(74) *Attorney, Agent, or Firm* — Coats & Bennett, PLLC

(57) ABSTRACT

A microchip oxygen sensor for sensing exhaust gases from a combustion process, and related methods. The microchip oxygen sensor includes a dielectric substrate and a heater pattern affixed to the substrate. A first electrode is affixed to the substrate and has a first plurality of fingers forming a first comb. A second electrode is affixed to the substrate and has a second plurality of fingers forming a second comb. The second electrode is disposed in spaced relation to the first electrode such that the first and second combs face each other. A semiconducting layer is disposed over the first and second electrodes so as form a physical semiconductor bridge between the first and second electrodes. The semiconducting layer comprises an n-type semiconducting material or a p-type semiconducting material. A porous dielectric protective layer, advantageously containing a catalytic precious metal, may cover the semiconducting layer.

8 Claims, 21 Drawing Sheets

Related U.S. Application Data

No. 12/980,725, filed on Dec. 29, 2010, now Pat. No. 8,586,394.

(60) Provisional application No. 61/299,487, filed on Jan. 29, 2010.

(51) Int. Cl.
 *G01N 27/406* (2006.01)
 *G01M 15/10* (2006.01)
 *F02D 41/04* (2006.01)

(52) U.S. Cl.
 CPC ...... *G01M 15/104* (2013.01); *G01N 27/4067* (2013.01); *F01N 2560/025* (2013.01); *F01N 2560/20* (2013.01)

(58) Field of Classification Search
 CPC .. F02D 41/2454; F02D 41/2474; F02D 41/28; F02D 11/107; F02D 2041/1409; F02D 2041/1419; F02D 2200/0406; F02D 41/0047; F02D 41/042; G01N 27/12; G01N 27/4067; G01N 27/4071; G01N 27/4175; G01N 27/419; G01N 33/007; F01L 1/024; F01L 1/34; F01L 2001/0537; F01L 2001/34436; F01L 2001/3444; F01N 13/009; F01N 13/0093; F01N 3/2026; F01N 2560/025; F01N 11/002; G01M 15/104

See application file for complete search history.

(56) References Cited

U.S. PATENT DOCUMENTS

| | | | |
|---|---|---|---|
| 4,276,600 A | 6/1981 | Hartford et al. | |
| 4,462,890 A * | 7/1984 | Touda | G01N 27/4071 204/425 |
| 4,500,412 A | 2/1985 | Takahashi et al. | |
| 4,535,316 A * | 8/1985 | Wertheimer | G01N 27/12 338/34 |
| 4,660,407 A | 4/1987 | Takami | |
| 4,744,344 A | 5/1988 | Morozumi | |
| 4,844,788 A * | 7/1989 | Takahashi | F02D 41/1455 204/406 |
| 4,980,044 A * | 12/1990 | Ker | G01N 27/4067 204/424 |
| 5,776,601 A * | 7/1998 | Fournier | C04B 41/5041 428/325 |
| 5,824,271 A * | 10/1998 | Frank | G01N 27/12 422/98 |
| 5,895,591 A | 4/1999 | Kojima | |
| 6,165,336 A * | 12/2000 | Maki | G01N 27/4074 204/415 |
| 6,181,026 B1 * | 1/2001 | Treharne | B60R 25/043 307/10.1 |
| 6,227,033 B1 | 5/2001 | Kainz | |
| 6,256,981 B1 | 7/2001 | Sullivan et al. | |
| 6,746,584 B1 | 6/2004 | Wang et al. | |
| 7,630,840 B2 * | 12/2009 | Sell | F02D 41/064 702/57 |
| 7,954,365 B2 | 6/2011 | White et al. | |
| 8,086,392 B2 | 12/2011 | Anilovich et al. | |
| 8,739,604 B2 * | 6/2014 | Krishna | G01N 27/4162 257/414 |
| 2002/0070112 A1 * | 6/2002 | Lee | G01N 27/4035 204/431 |
| 2003/0121801 A1 * | 7/2003 | Inaba | G01N 27/4075 205/785.5 |
| 2004/0060550 A1 | 4/2004 | Wu et al. | |
| 2005/0200448 A1 * | 9/2005 | Fujita | G01K 7/18 338/25 |
| 2008/0020504 A1 * | 1/2008 | Raghurama | B82Y 30/00 438/48 |

FOREIGN PATENT DOCUMENTS

| | | |
|---|---|---|
| JP | 4171803 B2 | 10/2008 |
| JP | 4607163 B2 | 1/2011 |
| WO | 20110093975 A3 | 8/2011 |

* cited by examiner

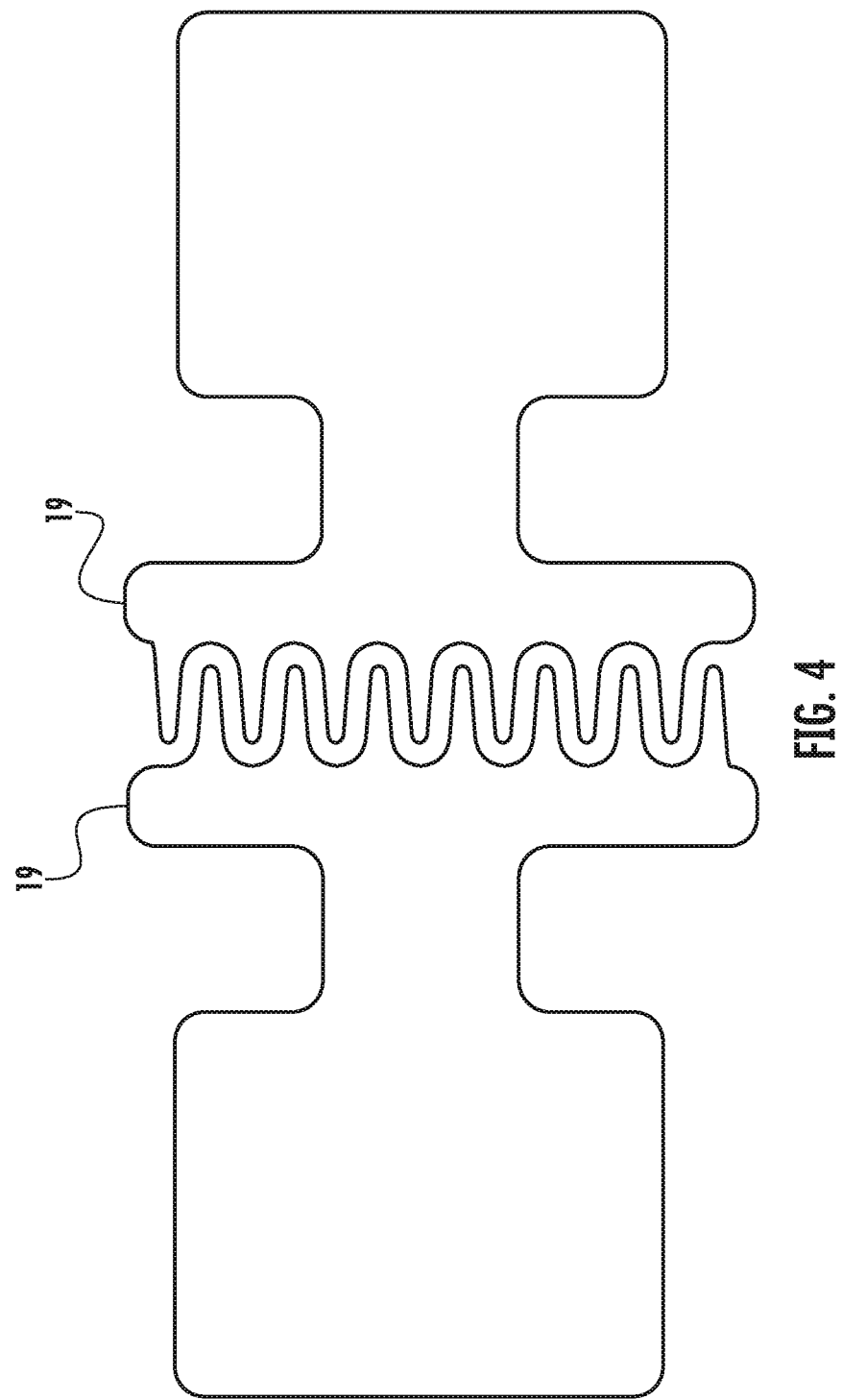

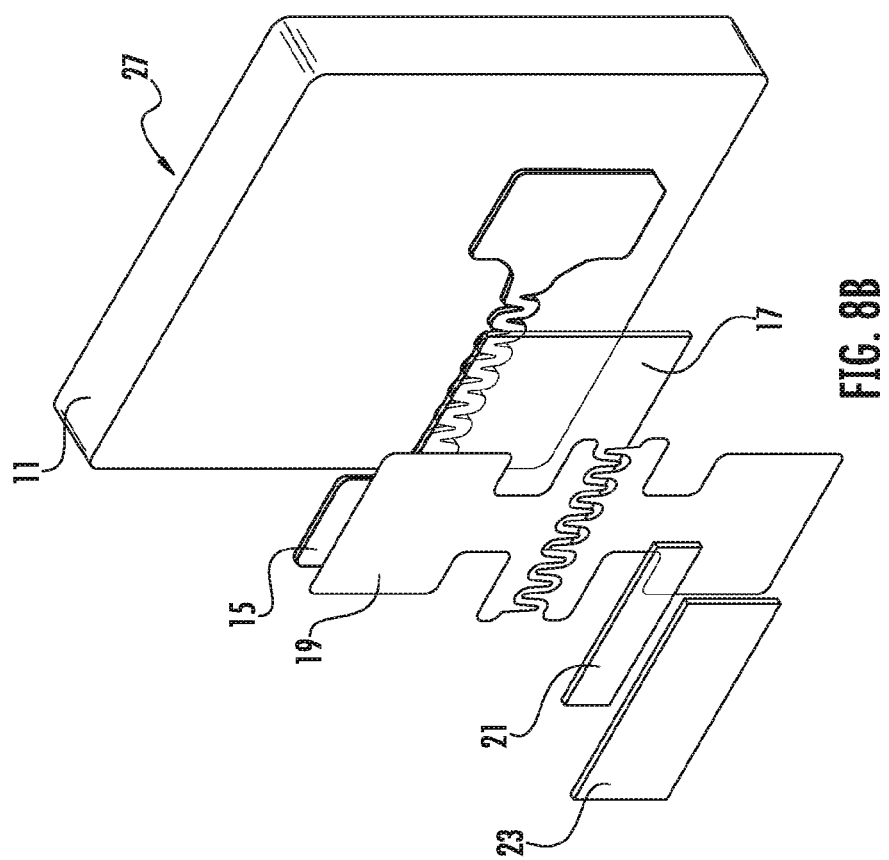
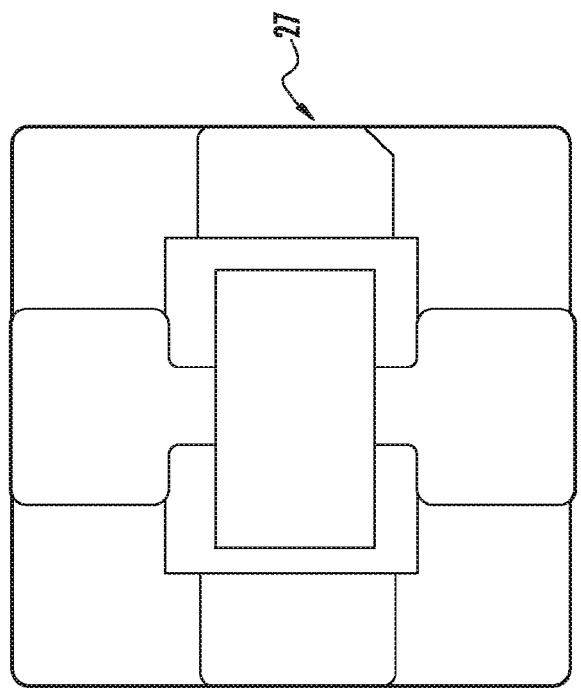

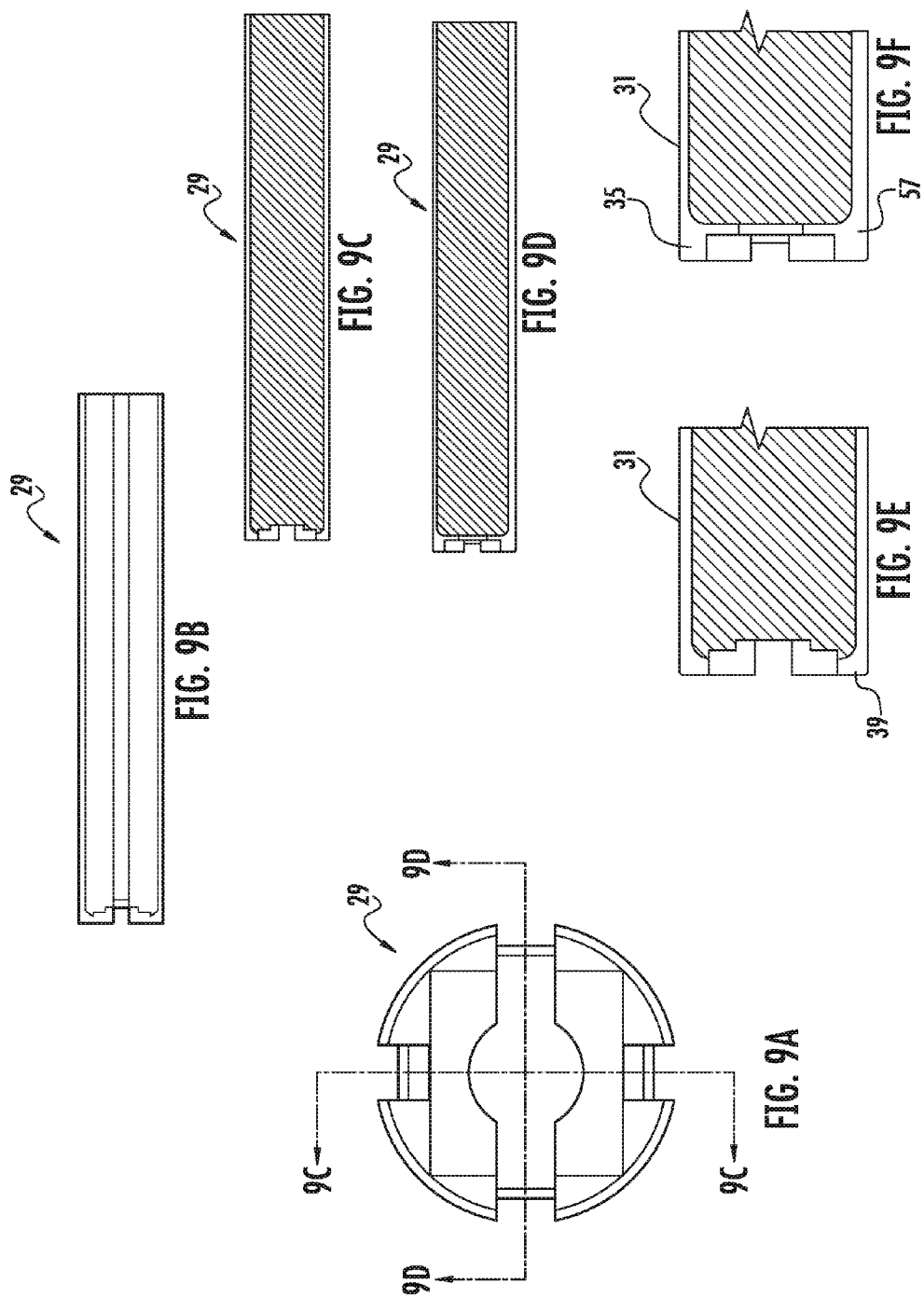

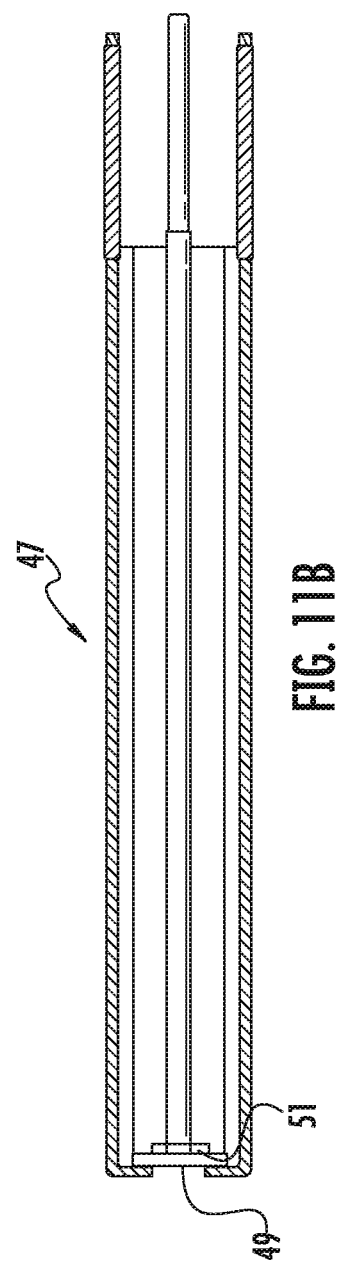
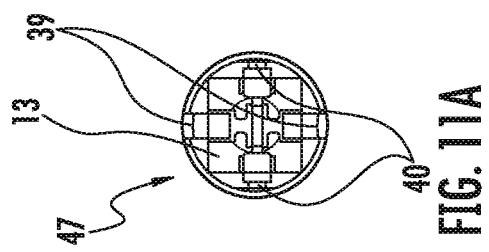

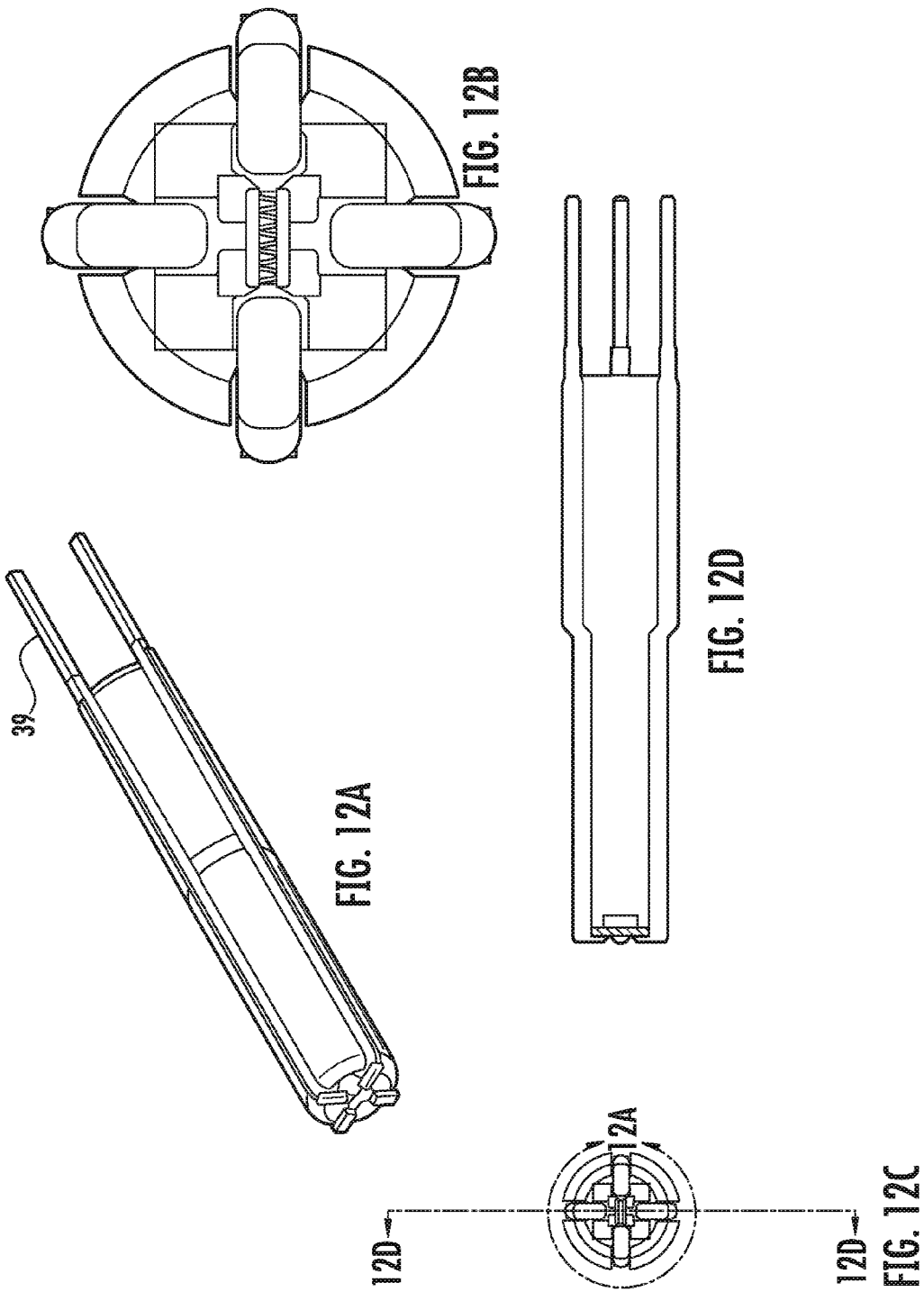

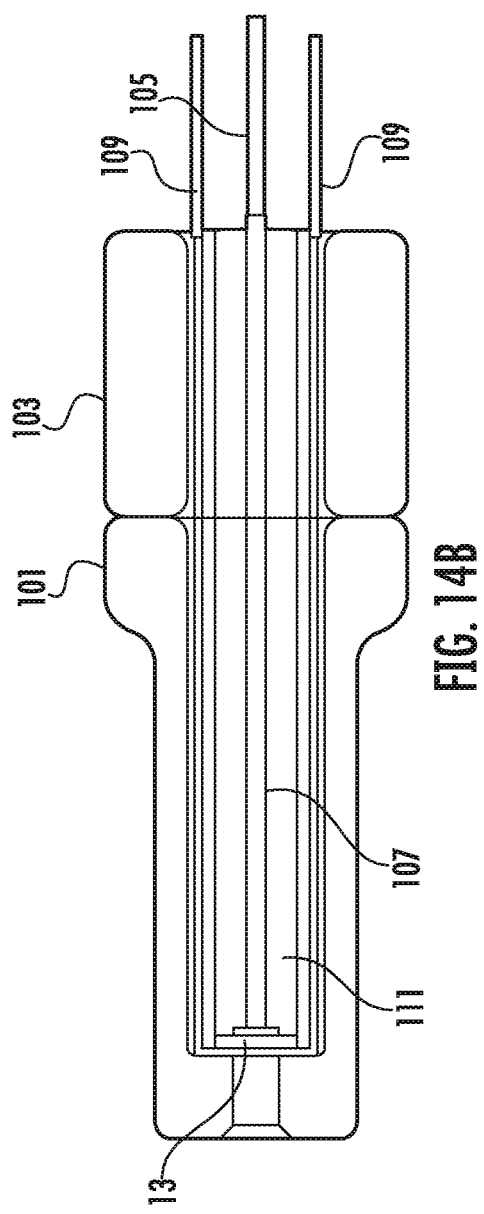
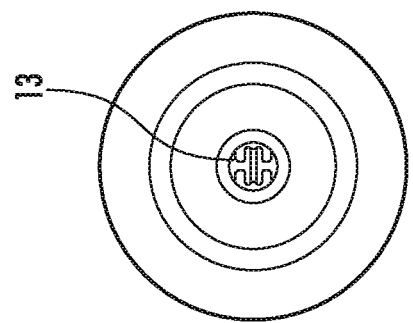

- APPLY DC VOLTAGE (V) BETWEEN $L_p$ AND $L_g$
- MEASURE VOLTAGE DROP ACROSS $R_2$ BETWEEN $L_S$ AND $L_G$
- VOLTAGE SHOULD BE STEADY BUT IN REALITY VARIES CONSIDERABLY BETWEEN 10V AND 16V.
- WISH TO VARY $R_2$ BASED ON VALUE OF APPLIED VOLTAGE PER EQUATION: $R_2 = 1098.9e^{-0.158V}$

MICROCHIP OXYGEN SENSOR FOR CONTROL OF INTERNAL COMBUSTION ENGINES OR OTHER COMBUSTION PROCESSES

This application is a continuation of U.S. patent application Ser. No. 14/073,182, filed 6 Nov. 2013, which is a continuation of U.S. patent application Ser. No. 12/980,725, filed 29 Dec. 2010, now U.S. Pat. No. 8,586,394, which claims the benefit of U.S. Provisional Application No. 61/299,487, filed 29 Jan. 2010, the disclosures of each of which are incorporated by reference herein in their entirety.

BACKGROUND

The present invention relates to oxygen sensors for sensing exhaust gases in an internal combustion engine or in any combustion process where control of the air-fuel ratio is desired. Of particular usefulness is the use of the sensors for control of small spark ignition engines such as those used in motorcycles, ATVs, recreational marine applications and unmanned air vehicles. In addition, the sensor is also suitable for individual cylinder control in multi-cylinder engines and hybrid engines for automotive and off-road applications. This invention may also be used as a safety device to trigger an alarm and/or disable combustion processes that produce rich exhaust gasses in enclosed spaces to prevent adverse conditions such as CO poisoning.

The utilization of closed loop control of internal combustion engines for reducing emissions and enhancing performance has gone through an evolutionary process since the 1970's with the replacement of carburetor based systems with single port (monotronic) fuel injection controlled by utilizing the signal from an unheated oxygen sensor to determine the engine's air/fuel ratio. This has evolved into multi-port fuel injection systems with heated oxygen sensors. Currently, such technology from the automotive industry is being applied to improve emission control in small engines for motorcycle and off-road applications. However, these sensors in their present state are cost prohibitive for a vast majority of global applications.

Two major classes of oxygen sensors have been developed and have competed for the automotive market since the onset of closed-loop control. Voltaic sensors rely on voltage generation due to a chemical potential across an ion conductor (stabilized zirconia) situated between the exhaust gas and a reference gas, typically air, in accordance with the Nernst equation, which is well known to those of ordinary skill. This type of sensor undergoes a step-wise change in voltage, transitioning across stoichiometry, due to an abrupt change in oxygen concentration at that point.

A second type of sensor known as a resistive sensor relies on a step-wise change in resistance of a semiconductor material (typically titania-based) as exhaust gases transition across the stoichiometric boundary. Both classes of sensors must be heated to become functional.

Zirconia sensors have held the majority of market share, and as such have gone through the greatest evolutionary change. Initially, zirconia sensors were unheated and relied on the heat from exhaust gasses to bring them to a temperature at which they become functional. Heater elements were later added to hasten sensor activation (light-off time), and increase the numbers of possible mounting locations along the exhaust stream. Further improvements have included the use of an integrated heater with multi-layer packaging technology, i.e., a planar sensor.

More recently universal "wide-band" or "air/fuel" sensors have been developed providing the ability to determine the air-fuel ratio away from stoichiometry in a somewhat linear current vs. air-fuel relationship, as compared to the step change in voltage at stoichiometry in earlier types of sensors. Unfortunately, these sensors are very expensive, have complicated circuitry, and the size reduction potential is limited due to the need to have enough charge carriers to generate a signal. As such, they are therefore not suitable for the small engine market. By "small engine" is meant as defined by the Environmental Protection Agency, " . . . those products rated less than or equal to 19 kilowatt (kW) (roughly equivalent to 25 horsepower [hp])" (Ref: Control of Emissions from Marine SI and Small SI Engines, Vessels, and Equipment—Final Regulatory Impact Analysis. EPA420-R-08-014, September 2008). This applies to single or multiple cylinder spark ignition or compression ignition engines, Rotary (Wankel) engines, or any other mechanical device utilizing the combustion of a fuel to convert chemical energy to mechanical energy regardless of particular mechanical system employed.

Resistive sensors by their nature can be reduced in size to a much greater extent than voltaic sensors. In accordance with the invention, this characteristic is used to make a sub-miniature "micro-chip" oxygen sensor of particular usefulness in the small engine market. The invention also enables the possibility of individual cylinder control in multi-port fuel injection systems for large spark ignition engines such as automobiles. Another use is to provide a safety cut-off sensor to ensure engines are not running rich and creating noxious gases.

SUMMARY

In accordance with one aspect of the invention, the sensor is made with a thin, typically, about 0.005" to about 0.015" in thickness, fully fired or partially (bisque) fired ceramic substrate or wafer made up primarily of aluminum oxide typically, i.e., about 94% to about 99.5% by weight, or other suitable dielectric material upon which multiple thin heater patterns for mass production of multiple sensor elements may be applied. Examples of other suitable dielectric materials include but are not limited to boron nitride, steatite (magnesium silicate), zirconium toughened alumina (ZTA), etc. These heater patterns are typically made of platinum, palladium, a combination thereof, or other suitable conductive material having an appropriate resistivity for the specific application.

The heater patterns may be fired to a high enough temperature, if necessary, to ensure adhesion and/or to achieve a suitable resistance value depending on the application technique employed. This firing may be delayed until later in the process. Typically, temperatures of about 650° C. to about 1400° C. constitute a high enough temperature. One or more dielectric layers is/are placed over this heater pattern to encapsulate and/or provide electrical isolation from the sensing portion of the sensor element to be applied in subsequent operations. This dielectric layer may also be fired to a suitable temperature to ensure adhesion and dielectric properties, if necessary, depending on the application technique employed. Typically, temperatures of about 650° C. to about 1400° C. constitute a high enough temperature.

Adjacent to this dielectric layer (either on top of or on the opposite side of the substrate) are placed two intermeshing "comb-shaped" electrodes of platinum, palladium, a combination thereof, or other suitable conductive material. Firing to a suitable temperature may be necessary depending on the application technique. An n or p type semiconducting material such as but not limited to $TiO_2$ or $Cr_2O_3$ based materials or other appropriate material is then applied to the electrodes in such a way as to cover and bridge a gap in the spaces between the intermeshing combs of the comb-shaped electrodes, followed by firing to a temperature and an amount of time necessary to sinter and achieve desired functional characteristics of the sensor. These functional characteristics include resistance under rich conditions, resistance under lean conditions, switch times going from rich to lean and lean to rich conditions, resistance to chemical poisoning, and the aging behavior or stability of the sensor (changes in these characteristics during the sensor's useful lifetime).

A porous protective dielectric layer may then be applied and fired to a suitable temperature sufficient to promote sintering and adhesion. By "porous" is meant sufficiently porous to allow the gases to readily pass through to the semiconducting material while preventing abrasion and poisoning. This protective layer may possess precious metal catalytic materials such as platinum, and/or palladium, and/or rhodium, as well as oxygen storage components such as cerium oxide or other suitable material as may be necessary to achieve the desired functional characteristics of the sensor. These catalytic materials may be part of the composition of the protective layer, or added as to impregnate the protective layer in a subsequent operation by applying a solvent containing dissolved or colloidal catalytic materials such as platinum, palladium, rhodium or any other suitable impregnant. At the end of these processes there results a wafer or substrate containing multiple oxygen sensor elements (chips), which are then singulated, i.e., divided out as single sensors via dicing, laser cutting, or other suitable techniques common to the semiconductor or electronics industry.

Each singulated chip element is then placed into an assembly, which is secured onto an exhaust system in such a way as to expose the sensing portion of the chip to exhaust gases. A voltage is applied to a heater circuit on the chip to bring the element to a temperature sufficient to activate the sensor. The resistance of the semiconducting portion of the element decreases with increased temperature, and either increases as it is exposed to higher levels of oxygen or decreases with increased oxygen, depending on the semiconducting material employed. By maintaining the element at an elevated temperature (above about 600° C.) the temperature effect is minimized and the condition of the exhaust gas can be determined by the step change in resistance at stoichiometry.

Four high temperature conductors are attached to the contact pads on the sensor element leading to wire connections that are connected to an electronic control unit (ECU) of the engine of the type which is conventional and of the type well known to those of ordinary skill in the art. The two wires from the heater circuit are used to apply a suitable voltage across the heater with one wire grounded (polarity does not matter) in order to heat the sensor to become active. Two wires from the sensor circuit of the chip element are connected to a circuit in the ECU. In one embodiment the step-wise resistance change can be measured directly by the ECU. In another, two resistors in a voltage divider circuit are used to enable the resistance changes in the sensor to be converted to a voltage signal between about 1 volt (rich) and about 0 volts (lean). This configuration enables matching the signal characteristics of conventional zirconia switching sensors. In reality, the signal is targeted to be slightly less than 1 volt and slightly greater than 0 volts, typically on the order of about 0.900V to 0.750V in rich condition to about −0.050V to 0.050V in the lean condition. With this measurement system configuration there is provided interchangeability between control algorithms for this sensor and conventional zirconia switching sensors.

In one or more embodiments, the present invention provides a microchip oxygen sensor for sensing exhaust gases from a combustion process. The oxygen sensor includes a dielectric substrate. A heater pattern is affixed to the substrate. A first electrode is affixed to the substrate and has a first plurality of fingers forming a first comb. A second electrode is affixed to the substrate and has a second plurality of fingers forming a second comb. The second electrode is disposed in spaced relation to the first electrode such that the first and second combs face each other. A semiconducting layer is disposed over the first and second electrodes so as form a physical semiconductor bridge between the first and second electrodes. The semiconducting layer comprises an n-type semiconducting material or a p-type semiconducting material. A porous dielectric protective layer may cover the semiconducting layer. The porous dielectric protective layer may contain a catalytic precious metal. The substrate may be disposed between the first and second electrodes and the heater pattern. The heater pattern may be disposed between the first and second electrodes and the substrate, with an additional dielectric layer disposed between the heater pattern and first and second electrodes. The combustion process may be associated with an internal combustion engine, with the heater pattern comprising platinum.

In one or more embodiments, the present invention provides a method sensing oxygen in exhaust gases from a combustion process. The method includes simultaneously heating a substrate of a microchip oxygen sensor and passing current through a sensing circuit of the microchip oxygen sensor; and also measuring a resistance of the oxygen sensing circuit. The heating the substrate involves passing a first current through a heater pattern affixed to the substrate. The sensing circuit includes a first electrode, a second electrode, and a semiconducting layer. The first electrode is affixed to the substrate and has a first plurality of fingers forming a first comb. The second electrode is affixed to the substrate and has a second plurality of fingers forming a second comb. The second electrode is disposed in spaced relation to the first electrode such that the first and second combs face each other. The semiconducting layer is disposed over the first and second electrodes so as form a physical semiconductor bridge between the first and second electrodes. The passing the current through the sensing circuit involves passing the current from the first electrode to the second electrode via the semiconducting layer. The combustion process may occur in a combustion chamber of an engine, with the oxygen sensor exposed to exhaust gases from the engine. The engine may be a multi-cylinder engine. The measuring the resistance of the oxygen sensing circuit may include applying a voltage to the oxygen sensor via a voltage divider circuit contained in a wire harness connector operatively disposed between the oxygen sensor and an electronic control unit of the engine. The measuring the resistance of the oxygen sensing circuit may include applying a voltage to the oxygen sensor via a voltage divider circuit contained in an electronic control unit of the engine. The semiconducting layer may include a p-type semiconducting material, and the method may further include performing at least one of following in response to detecting rich exhaust gases based on a resistance of the oxygen sensor: generating an alarm and disabling the combustion process.

These and other advantages and features that characterize the invention are set forth in the claims annexed hereto and forming a further part hereof. However, for a better understanding of the invention, and of the advantages and objectives attained through its use, reference should be made to the Drawings, and to the accompanying descriptive matter, in which there are described exemplary embodiments of the invention.

BRIEF DESCRIPTION OF THE DRAWINGS

FIG. 4 is a schematic view of configuration for a potential electrode is a "comb" pattern, which is the third layer of the wafer of FIG. 1, to be applied over the dielectric layer of FIG. 3 at a 90 degree orientation to the heater pattern of FIG. 2, or applied to the substrate on the opposite side of the heater pattern.

FIG. 8A and FIG. 8B are a schematic side view and an exploded perspective view, respectively, of a second individual element assembly, having the heater and sensor circuits on the same side of the element substrate (chip).

FIG. 9A-F are schematic views of an inner ceramic insulator upon which the element assembly with attached conductors of FIG. 10 is placed.

FIG. 11A and FIG. 11B are a schematic end view and side view (in cross section), respectively, of the element assembly of FIGS. 9A-F, positioned on the end of the inner ceramic insulator of FIGS. 8A-B, and having conductors terminals of FIGS. 10A-E attached to contact pads on the element having heater and sensor circuit on opposite sides of the element substrate (chip).

FIGS. 12A-D are schematic views of the element assembly of FIGS. 7A-B or FIGS. 8A-B, positioned on the end of the inner ceramic insulator, and having conductor terminals attached to contact pads on the element having heater and sensor circuit on the same side of the element substrate (chip).

FIGS. 14A-B are schematic views of the sub assembly containing the element/conductor sub assembly of FIGS. 10A-E along with the insulators of FIGS. 9A-F.

DETAILED DESCRIPTION

Figure 1:
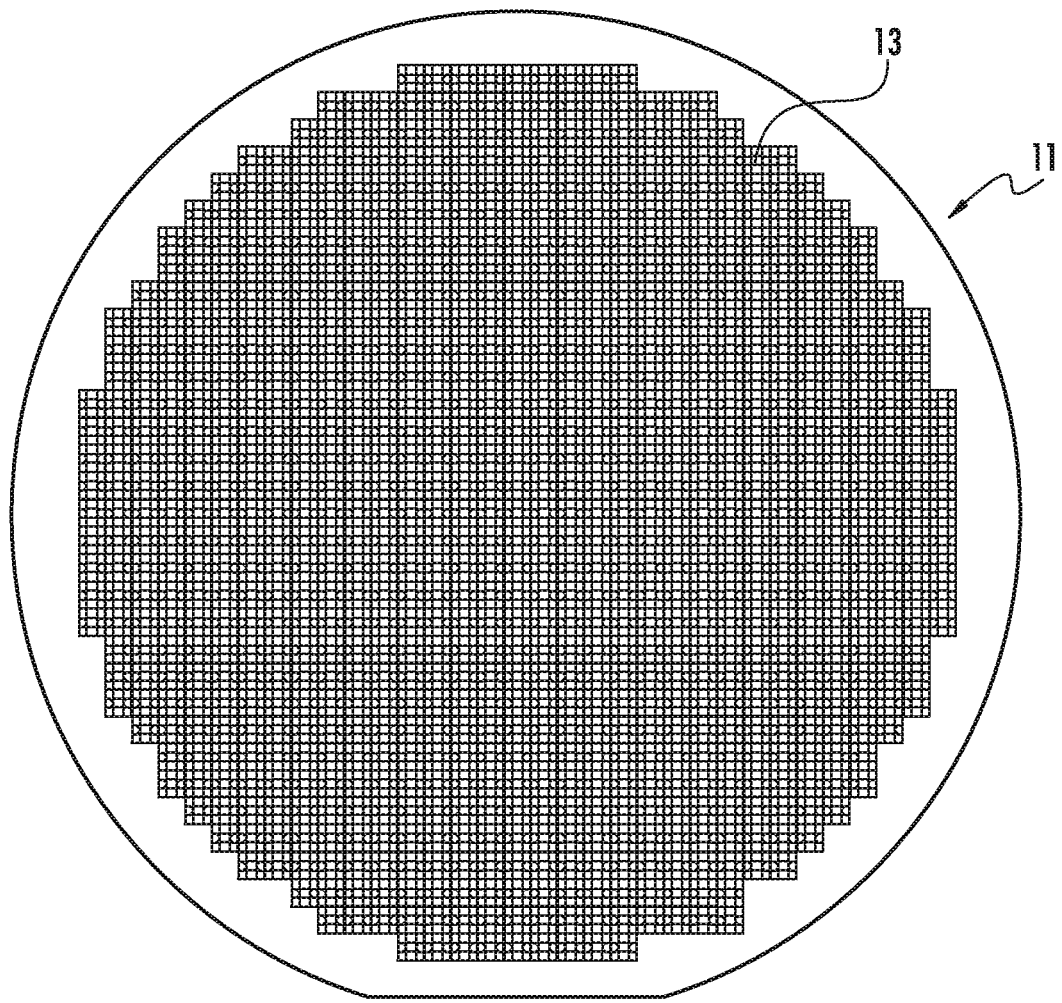
FIG. 1 is a schematic view of a ceramic substrate or wafer having multiple elements applied in a pattern suitable for singulation, i.e., separate out single elements.

As shown in FIG. 1, for purposes of illustration only and not limitation, the present invention includes a thin, typically about 0.005" to about 0.015" thick ceramic substrate or wafer 11 made primarily of aluminum oxide in a ratio of about 94% to about 99.5% by weight, or other suitable dielectric material upon which multiple elements may be produced by first applying thin heater patterns composed of platinum, palladium, a combination thereof, and/or other suitable materials, and placed thereon. Such suitable dielectrics include but are not limited to boron nitride, steatite (magnesium silicate), zirconium toughened alumina (ZTA), etc. . . .

Figure 2A:
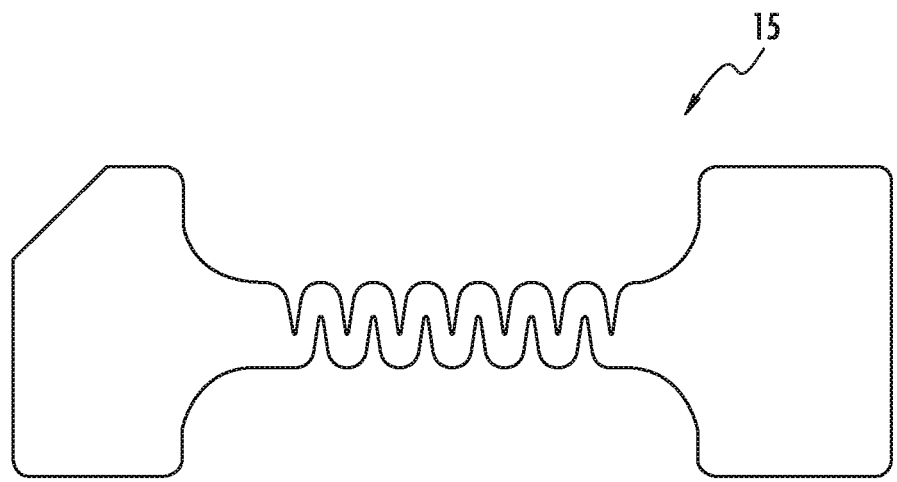
FIG. 2A and FIG. 2B are a schematic side view and perspective view, respectively, of a potential heater pattern having a predetermined thickness to be applied as a first layer to the substrate of FIG. 1.
Figure 2B:
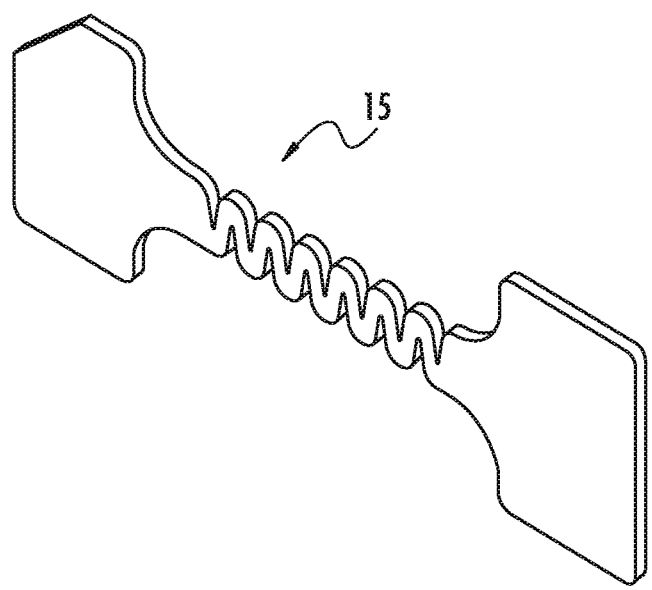

The heater patterns, as shown in FIG. 2, can be applied using physical vapor deposition (electron beam or sputtering) or electroless plating, then masking using photolithography techniques followed by chemical etching. Alternatively, the heater pattern 15 can be applied by first masking the substrate using photolithography techniques, then applying the platinum, palladium, or other suitable heater material using the techniques described above and removing the mask to leave the heater patterns on the substrate. Typical thicknesses of this metal layer making up the heater are between 25 and 1250 nm as needed to achieve desired resistance values. It is also understood by those familiar with the art, that often a thin (5 to 15 nm thick) coating of titanium, vanadium or other suitable material may be applied between the metal (Pt, Pd, etc.) and adjacent layers (substrate, cover layers, etc.) to improve adhesion. An example of a heater pattern 15 is illustrated in FIG. 2, but it need not be limited to such configuration. In one embodiment, it may be suitable to fire the heater pattern to elevated temperatures of between about 650° C. and about 1450° C. and hold for 0.25 to 6 hrs. at some point in the manufacturing process to improve adhesion and/or achieve desired electrical resistivity as a result of sintering.

Figure 3A:
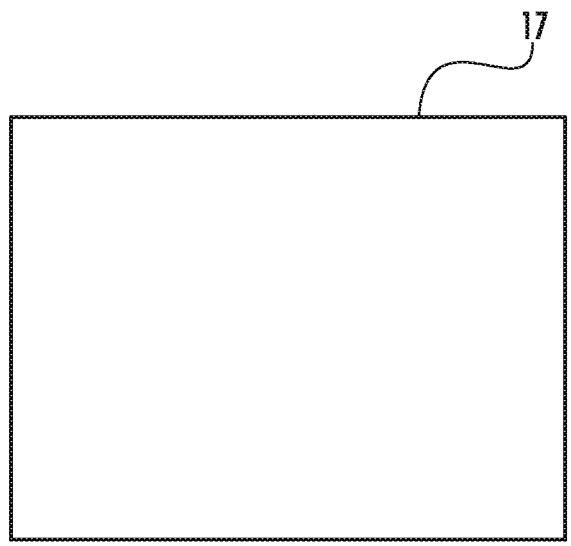
FIG. 3A and FIG. 3B are a schematic side view and perspective view, respectively, of one or more dielectric layer(s) to be applied over the heater pattern as a second layer on the wafer in FIG. 1, also having a predetermined thickness.
Figure 3B:
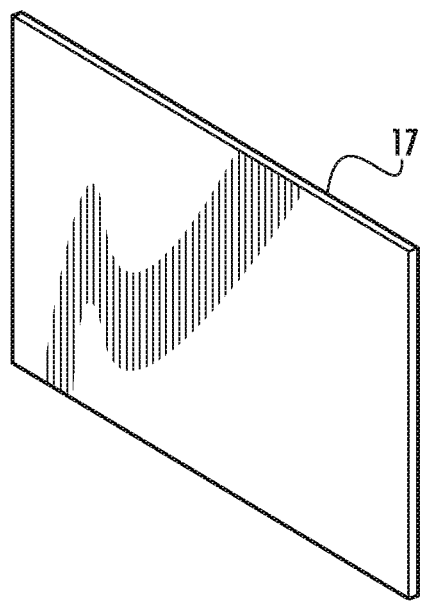

Following the application of the heater patterns 15, an electrically insulating layer 17 as shown in FIG. 3, and composed primarily of $Al_2O_3$ or other suitable dielectric material is applied via screen printing, using Direct-Write Technology (DWT), ink-jet printing, or using photolithography masking and vapor deposition techniques or vapor deposition and etching techniques. Direct Write Technology involves dispensing a liquid or a paste material (in this case dielectric in an organic carrier) through a needle or other small orifice with the aid of a computer controlled positioning and dispensing unit with deposition control in three axes. Following the application of the insulating dielectric layer 17, firing to an elevated temperature between about 650° C. and about 1400° C. is performed as necessary to sinter and/or improve adhesion.

The comb shaped electrodes 19 shown in FIG. 4 are preferably made of platinum, palladium, a combination thereof and/or other suitable conductor material. The electrodes are applied with the contact pads at 90 degrees from the heater contact pads on either the same side of the substrate as the heater pattern, or on the opposite side. These electrode patterns 19 are applied using photolithography masking and either vapor deposition or electroless plating as is suitable. Following application, photo resist is removed and the electrodes are fired at an elevated temperature of between about 650° C. and about 1400° C. and hold for 0.25 to 6 hrs. to improve adhesion and adjust electrode conductivity.

Figure 5A:
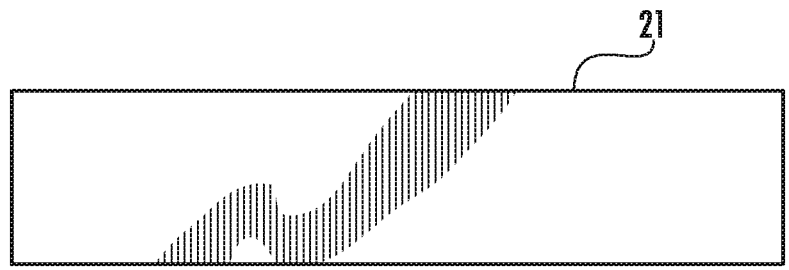
FIG. 5A and FIG. 5B are a schematic side view and perspective view, respectively, of semiconducting material of predetermined thickness to be applied in a pattern over the electrodes of FIG. 4 in such a way as to bridge a gap between the combs, with the semiconductor pattern being the fourth layer on the wafer of FIG. 1.
Figure 5B:
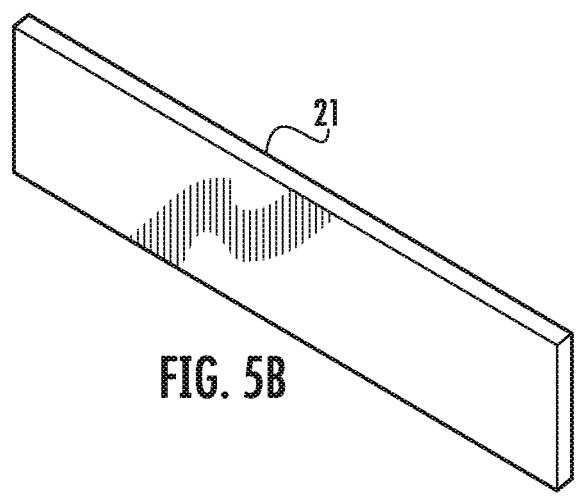

An n-type or p-type semiconductor bearing material 21 such as $TiO_2$ or $Cr_2O_3$ as shown in FIG. 5 is applied to the electrodes 19 to a suitable thickness typically between 5 and 150 microns to cover and bridge the gap between the combs of the electrodes 19. The material may be applied as a paste using screen printing, ink-jet printing, or Direct Write Technology as is appropriate. Following application, the wafer is dried to a temperature of approximately 90 to 125° C. for 0.5 to 6 hrs. and fired to an elevated temperature between about 650° C. and about 1300° C. and hold for 0.25 to 6 hrs. to remove organic carrier materials, sinter, and improve adhesion. Alternatively, this layer may also be applied using photolithography masking and vapor deposition techniques.

Figure 6A:
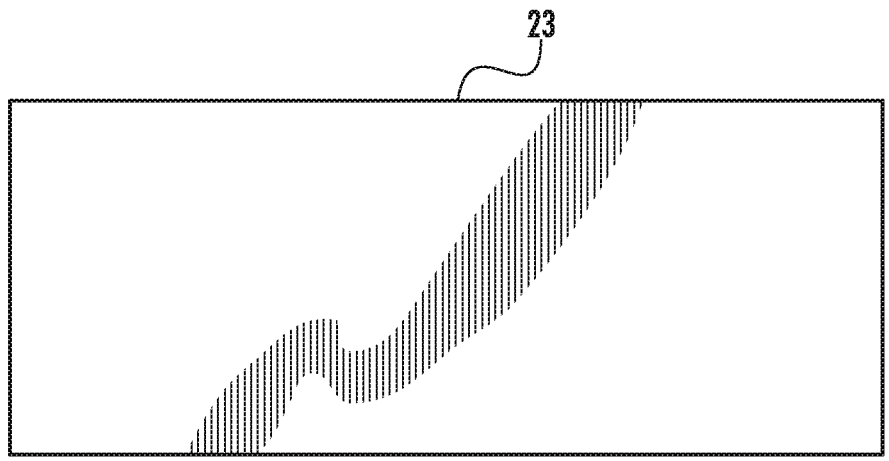
FIG. 6A and FIG. 6B are a schematic side view and perspective view, respectively, of the porous dielectric protective layer to be applied over the semiconducting layer, and is the fifth layer on the wafer of FIG. 1.
Figure 6B:
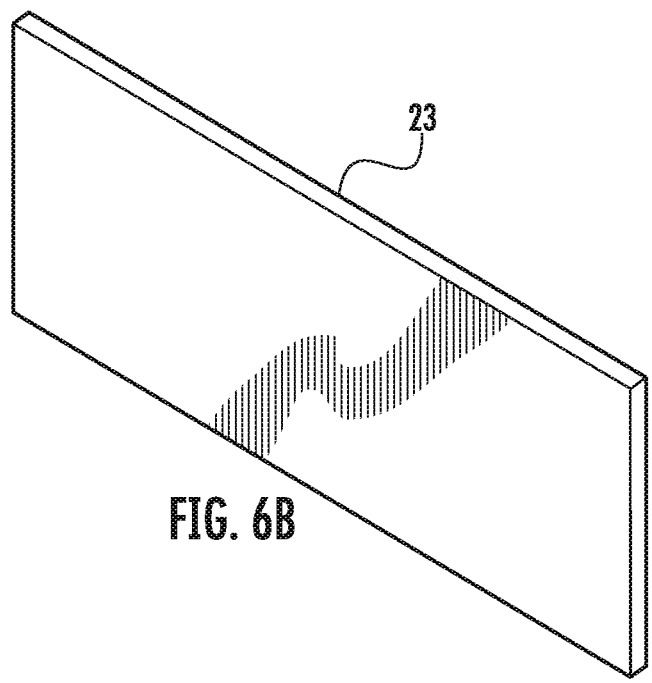

A porous dielectric paste material 23 as shown in FIG. 6 which is composed of organic carriers common in the printing industry, with solids such as Aluminum Oxide based compositions, or spinel (magnesium alum inate) is applied over the semiconducting material using, screen printing, ink-jet printing, or Direct Printing Technology to a thickness of between about 5 and about 150 microns. Following the application of this material it is dried at temperatures of approximately 90 to 125° C. for 0.5 to 6 hrs., then fired to a temperature between about 650° C. and about 1100° C. and held for 0.25 to 6 hrs. This material may possess catalytic materials such as platinum, and/or palladium, and/or rhodium, and/or an oxygen storage component such as $Ce_2O_3$ in concentrations suitable to achieve the desired functional behavior of the sensor. Alternatively, these catalytic materials may be applied after firing using an impregnant applied manually or robotically using a syringe or applied using Direct Printing Technology.

Figure 7B:
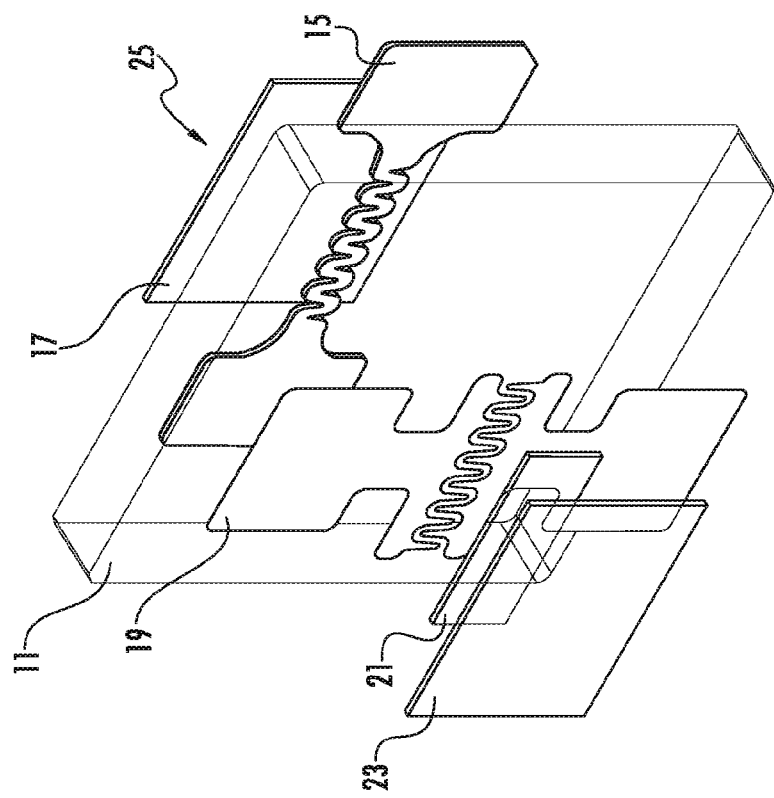
FIG. 7A and FIG. 7B are a schematic view and an exploded perspective view, respectively, of a first individual element assembly, having the heater and the sensor circuits on the opposite sides of the element substrate (chip).
Figure 7A:
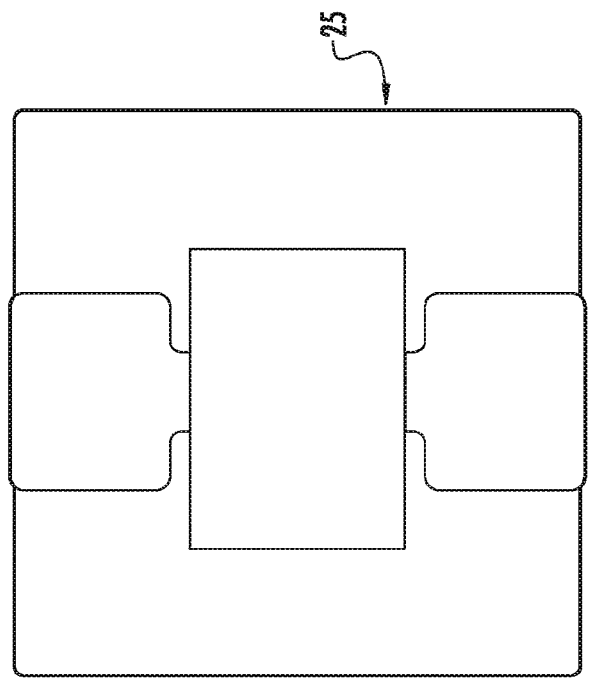
Figure 10A:
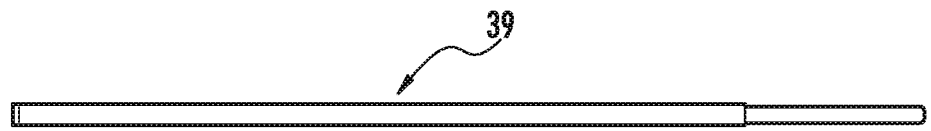
FIGS. 10A-E are schematic views of conductor terminals used to connect the sensor element and heater circuits of FIG. 7A or 7B to wires leading to the electronic engine/combustion control system.
Figure 10B:
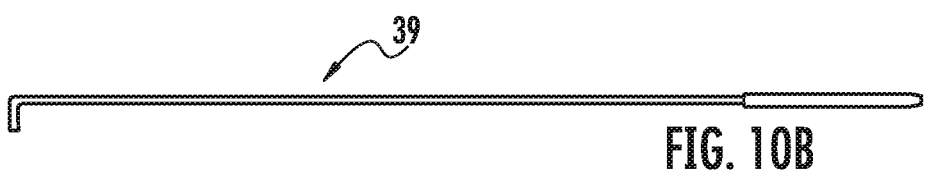
Figure 10C:
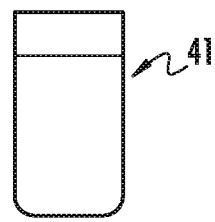
Figure 10D:
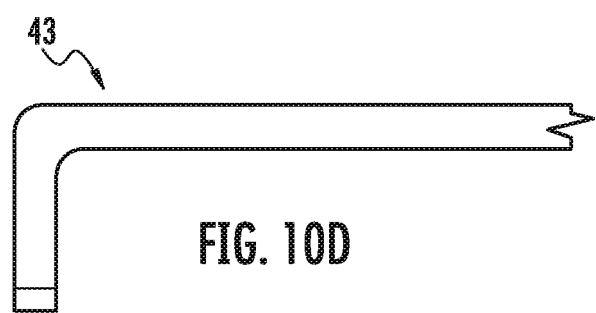
Figure 10E:
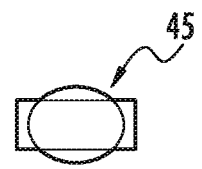
Figure 13A:
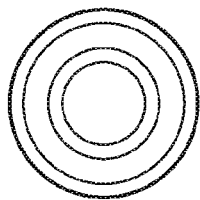
FIGS. 13A-G are schematic views of a two-piece outer ceramic insulator which is placed over the sub-assembly of FIGS. 8A-B.
Figure 13B:
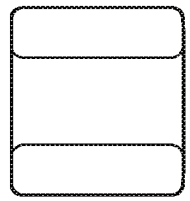
Figure 13C:
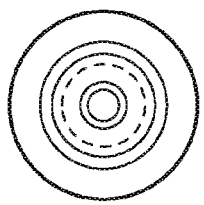
Figure 13D:
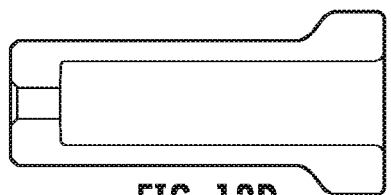
Figure 13E:
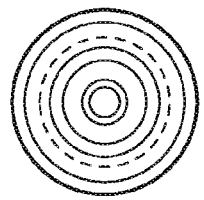
Figure 13F:
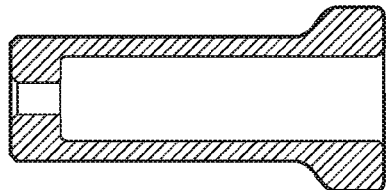
Figure 13G:
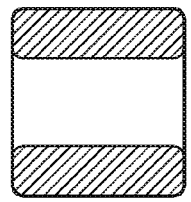

FIGS. 7 and 8 are schematic views of two versions of complete sensor elements 25 and 27 with all layers illustrated. As may be appreciated from the foregoing discussion, the main components of the sensor have been discussed and illustrated. However, as will be readily apparent to those of ordinary skill, for the platinum layer it may be desirable to add a thin layer, typically about 5 to about 15 nanometers, of titanium (optional) or vanadium or other pure suitable material to both sides of each platinum layer to promote adhesion to the aluminum oxide layer. Thus, a typical sequential arrangement of layers is as follows:

| Item | Version 1 (FIG. 7) | Version 2 (FIG. 8) |
| --- | --- | --- |
| Aluminum oxide substrate (11) | Side A | Side A |
| Titanium | Side A | Side A |
| Platinum heater (15) | Side A | Side A |
| Titanium | Side A | Side A |
| Dielectric (17) | Side A | Side A |
| Titanium | Side B | Side A |
| Platinum electrode (19) | Side B | Side A |
| Titanium | Side B | Side A |
| Semiconductor (21) | Side B | Side A |
| Porous Cover Layer (23) | Side B | Side A |

The sensor assembly 29 is now described. As shown in FIG. 9, on the tip of the inner ceramic part, there is a recess whose length and width is slightly larger than the element chip, and whose depth is slightly smaller than the chip to allow for positioning and securing the chip in the assembly and allowing for typical dimensional tolerances found in production. There is also a gap along the centerline of the inner ceramic to avoid contact of the center portion of the chip to promote thermal isolation immediately adjacent to the heated portion in the center of the chip. The element chip of FIG. 7 is positioned on the center of the end of the inner ceramic in the recess. Current carrying conductors or terminals 39 of FIG. 10 made of materials suitable for the operating environment, i.e., the temperature and exhaust gas atmosphere (ex.: Inconel 600, Inconel 625, etc. . . . ), are then attached to the four contact pads of the chip and commuted through the grooves in the outer edges of the inner ceramic as shown in FIGS. 11 and 12. FIG. 11 also shows a sensor side 49 and heater side 51. Securing terminals to the contact pads for improved electrical contact may be achieved using a high temperature conductive paste (Pt, Pd, etc.), high temperature brazing, laser welding, or may simply be done by providing a mechanical contact assembly. This sub assembly is then inserted into a two-piece outer insulator of FIG. 13, which has a hole for exhaust gases to reach the sensing portion of the chip as shown in FIG. 14.

Figure 15A:
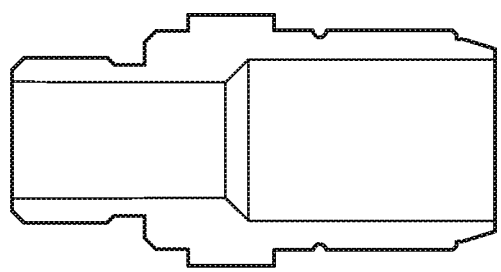
FIGS. 15A-C are schematic views of a threaded metal housing.
Figure 15B:
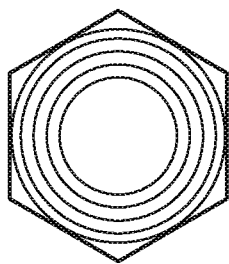
Figure 15C:
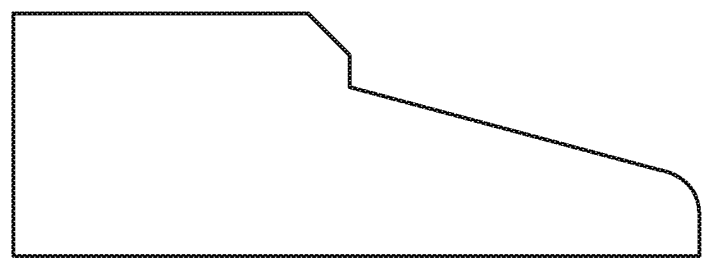
Figure 16A:
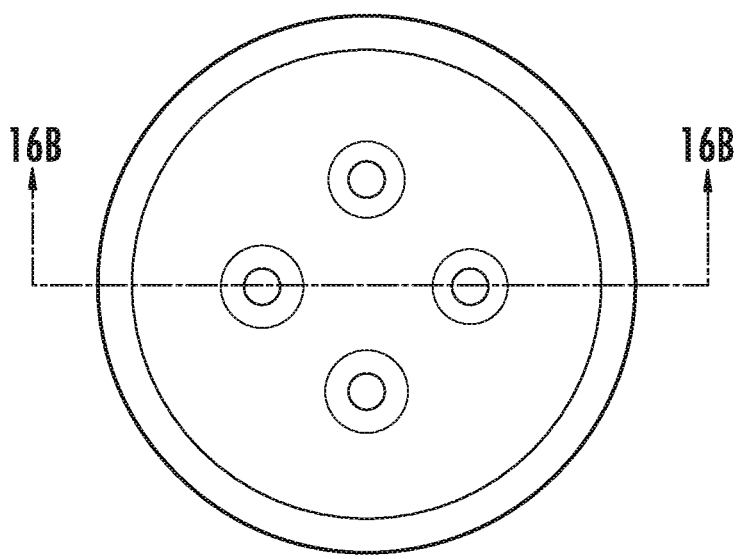
FIGS. 16A-C are schematic views of an insulating disk having passages through which conductors may pass.
Figure 16B:
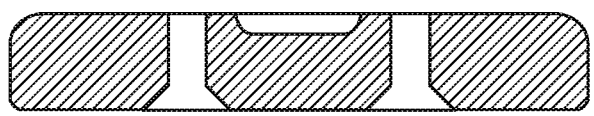
Figure 16C:
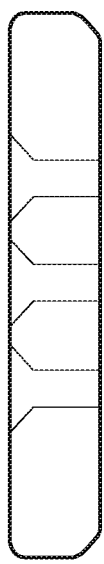
Figure 17:
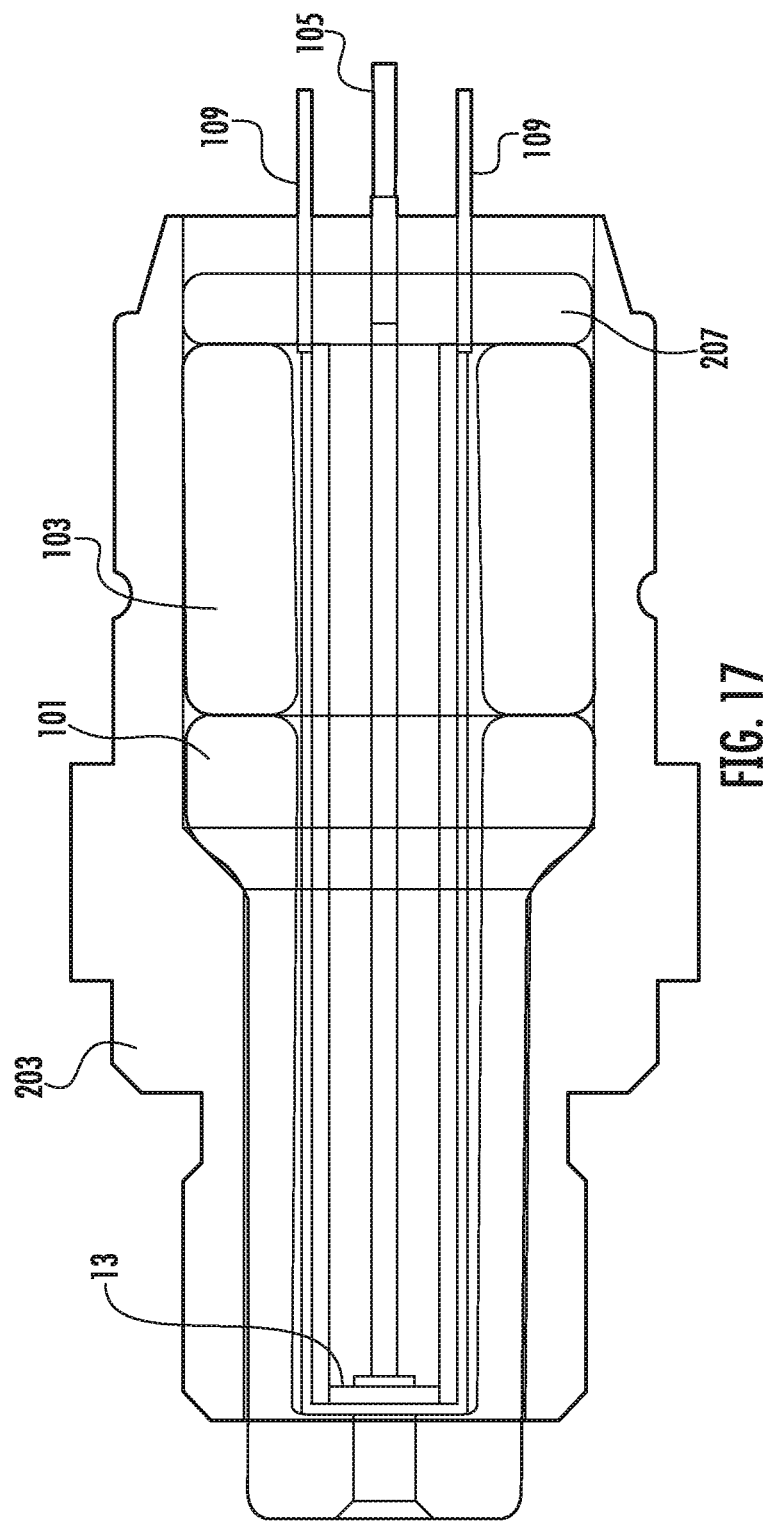
FIG. 17 is a schematic side cross section view of the sensor assembly.

This outer ceramic insulator 101, 103 of FIG. 13 also provides mechanical security and electrical insulation for the conductive terminals. There are two outer diameters on the first outer ceramic part 101 which will be used to seat the ceramic sub-assembly in a metal housing of FIG. 15. The second outer ceramic 103 is a bushing having the same inner diameter, and the larger outer diameter of the first part. The sensor element 13, an inner insulator 107, heater terminals 105, signal terminals 109, and inner insulator 111 are also shown. This metal housing or "shell" shown in FIG. 15 has an internal transition feature, which mates to the outer ceramic part and has a suitable standard thread and hexagonal faces of suitable size for installation into an exhaust pipe. The ceramic sub-assembly is placed into the shell, small amounts of high temperature potting material are placed around each conductor, and a thin round ceramic wafer or disk of FIG. 16 having holes of appropriate geometry is then placed over the conductors and pushed into place against the end of the two concentric ceramic parts. The back end of the shell is then crimped to secure all components of the assembly as shown in FIG. 17. This assembly shows an outer shell 203 and cement seal 201. This assembly may require further heat treatment as may be necessary to cure the potting material used for sealing.

Figure 18:
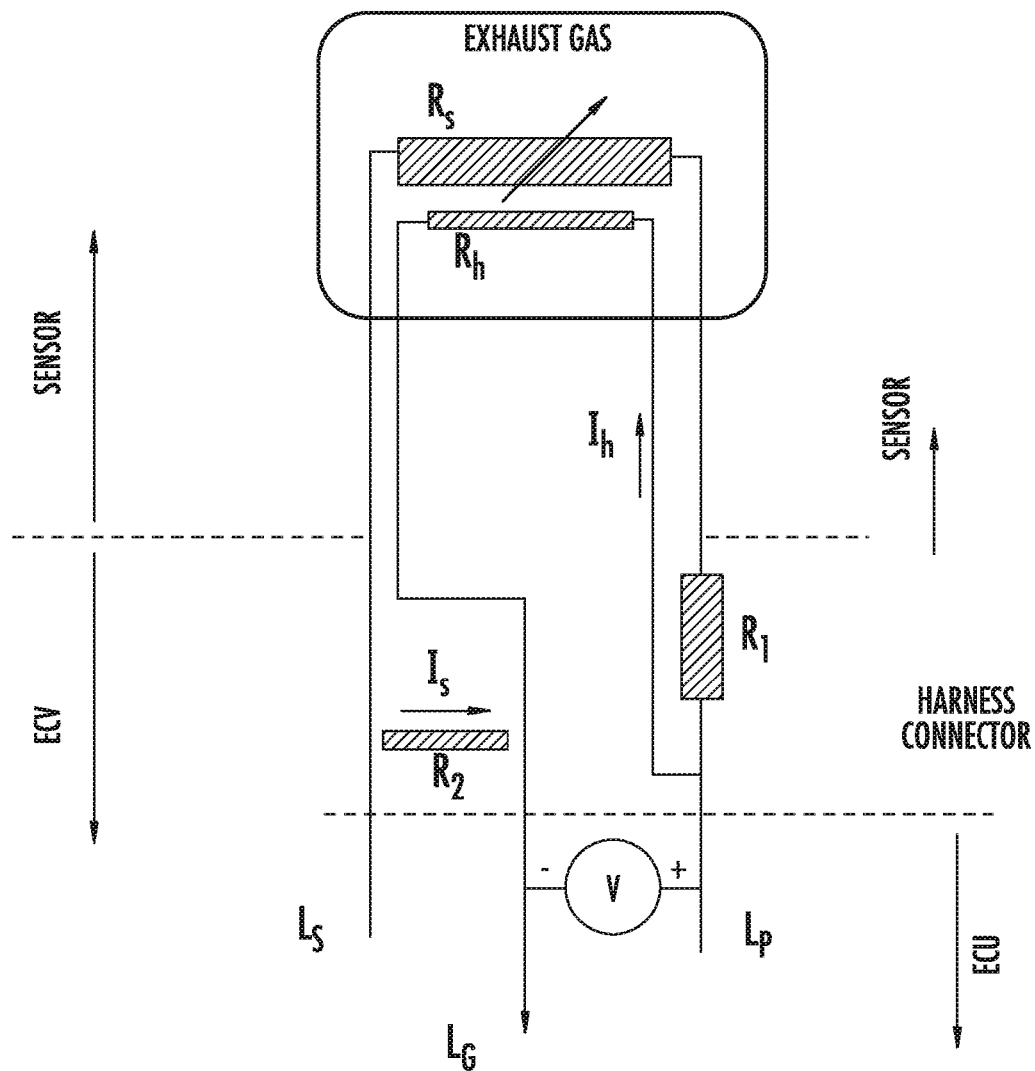
FIG. 18 is a schematic view of a sensor electrical connection including a voltage divider circuit, which may be placed in a connector housing or in an electronic control unit, is used for sensing oxygen in exhaust gases.

The circuitry of the invention may be used for a number of applications. The oxygen sensor may be used for engine control. In one illustrative embodiment, FIG. 18 illustrates a sensor along with a voltage divider circuit that may or may not be employed depending upon the particular application. This voltage divider circuit can be physically located either in an electronic control unit or in a harness connector as may be appropriate for the application. It may also be incorporated in the sensor assembly or on the sensor element itself; however, this may not be practical due to the high temperatures reached in the sensor may adversely influence the resistance values of the voltage divider over time. The material chosen for the element sensor resistor ($R_s$) is chosen to be an n-type material which increases in resistance with increasing oxygen in exhaust gases. A voltage, V, typically between about 5V and about 18V is applied to the heater circuit ($R_h$) to heat the sensor element resistor ($R_s$) to a temperature at which the sensor becomes active, such that the sensor circuit resistance responds to changes in the level of oxygen in the exhaust gas. That same voltage may be applied to voltage divider circuit ($R_1/R_s/R_2$), or a separate and different voltage may be applied. Signal stability and therefore, performance is improved by regulating the voltage applied to this circuit to a stable level. The ratio of $R_2$ to $R_1$ is chosen based upon the applied voltage, and is typically the same as or near the applied voltage (e.g., 12:1 for 12 volts, 14:1 for 14 volts, etc. . . . ). The value chosen for $R_2$ (and therefore R1 also) is dependent upon the system such that the voltage measured in the lean condition stays below the target value, typically <100 mV, for the particular system. Both of these values are dependent upon the resistive characteristics of the element under the operating conditions, therefore the location of the sensor in the exhaust stream may have an impact on the resistance values chosen.

Figure 19:
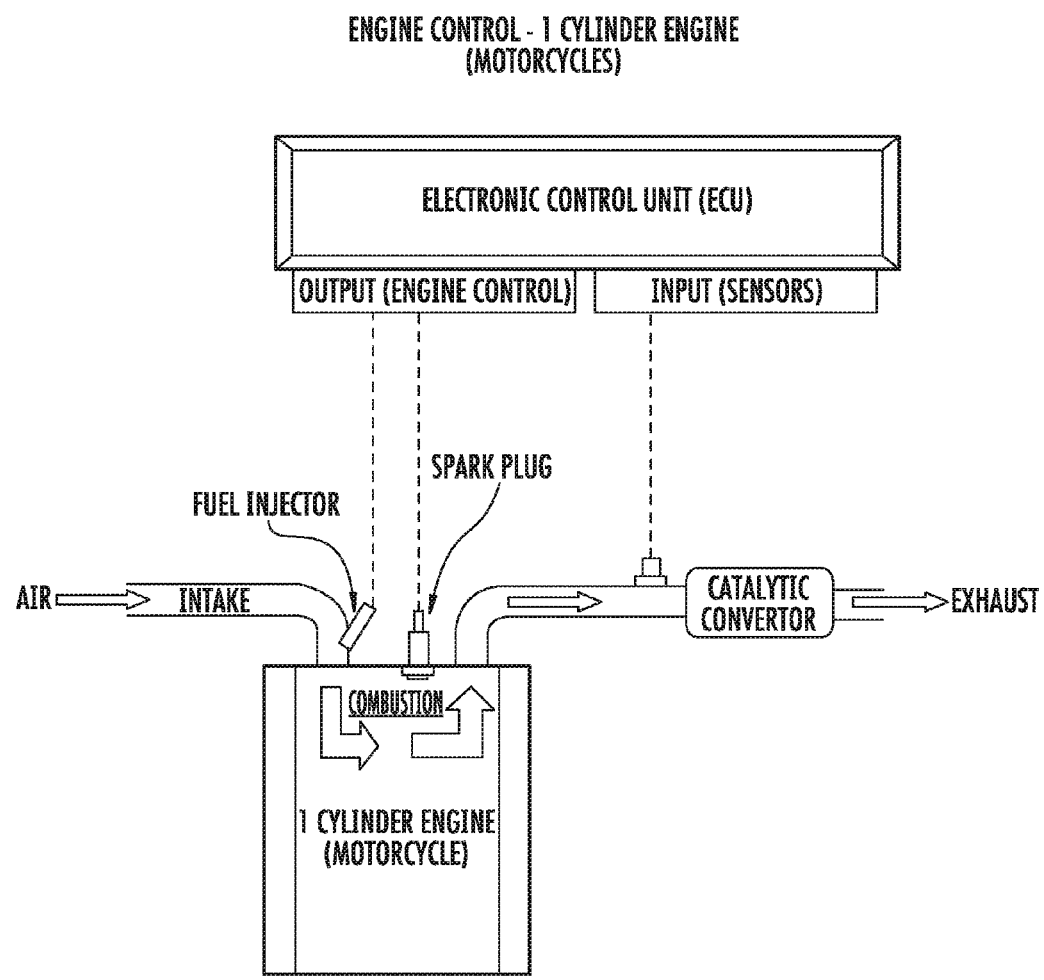
FIG. 19 is a schematic view of the use of the invention in a one-cylinder engine application.
Figure 20:
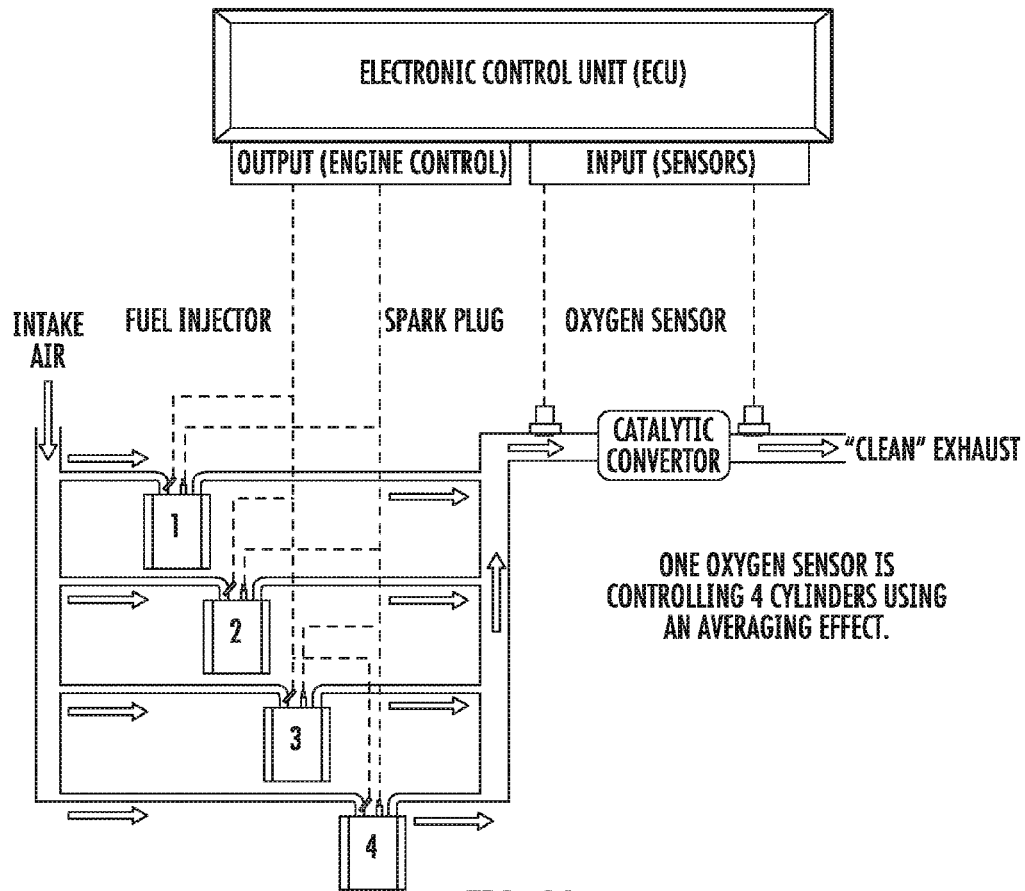
FIG. 20 is a schematic view of the current industry's use of oxygen sensors in multi-cylinder engine applications.
Figure 21:
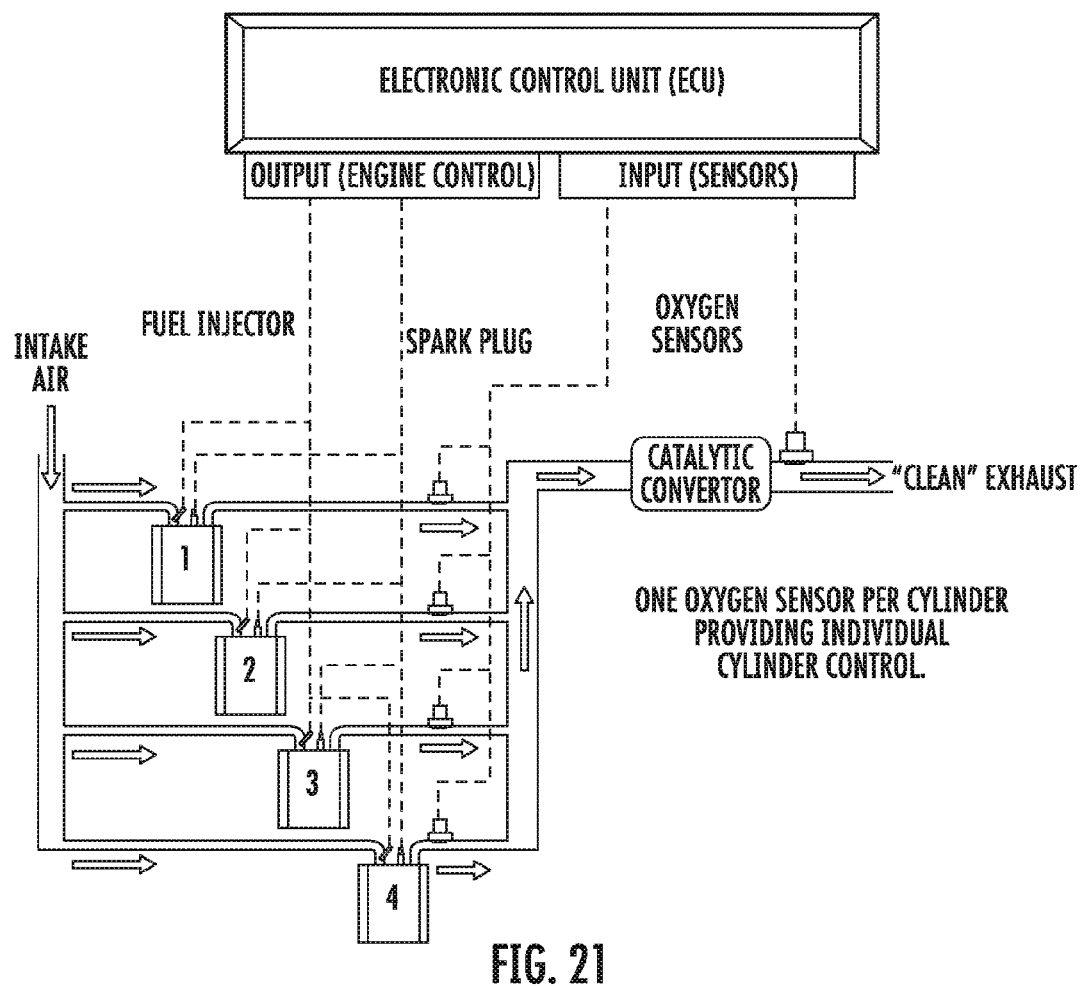
FIG. 21 is a schematic view of the use of the invention in multi-cylinder engine applications for individual cylinder control.

FIG. 19 illustrates a use of the device of the invention for engine control for a one (1) cylinder engine, for example, for a motorcycle. FIG. 20 illustrates engine control in a multi-cylinder environment according to the prior art where one oxygen sensor controls four (4) cylinders using an averaging effect. FIG. 21 illustrates a use of the device of the invention wherein one (1) oxygen sensor is provided per cylinder in a multi cylinder engine providing individual cylinder control.

The device may also be used as a safety switch. More specifically, in another embodiment, the invention may be used as a safety switch for engines designed to run lean in an enclosed environment to prevent the generation of toxic gases such as CO. By selecting a p-type semiconducting material, e.g., $Cr_2O_3$, instead of an n-type material, e.g., TiO2, the resistance is low in lean exhaust environments and high in rich exhaust gas environments. For instance, many propane powered devices (floor buffers, burnishers, Zamboni™, etc.) require a sensor to detect when the engine begins to run rich creating, carbon monoxide and other noxious gases this sensor would be used to sense the condition triggering an engine shut-down and/or an alarm. Some companies use oxygen sensors for this purpose; however, they are not well suited for these applications as they are too large and expensive. A voltage divider circuit may or may not be employed depending on the particular application.

The ability to produce these sensors in very small sizes (micro-chip size) with significant reduction in cost of production along with the greatly reduced power requirements as compared to conventional oxygen sensors used in the automotive industry makes this technology ideally suited for the motorcycle and small engine markets. Additionally, these same features provide an opportunity for utilizing one sensor per cylinder on multi-cylinder applications, e.g., automobiles and compressed natural gas power generators, for individual cylinder control emission strategies.

While the present invention has been illustrated by a description of various embodiments and while these embodiments have been described in considerable detail, it is not the intention of the Applicant to restrict, or any way limit the scope of the appended claims to such detail. The invention in its broader aspects is therefore not limited to the specific details, representative apparatus and method, an illustrative example shown and described. Accordingly, departures may be made from such details without departing from the spirit or scope of Applicant's general inventive concept.

What is claimed is:

1. A method of sensing oxygen in exhaust gases from a combustion process, comprising:
   simultaneously heating a substrate of a microchip oxygen sensor and passing current through a sensing circuit of the microchip oxygen sensor;
   measuring a resistance of the oxygen sensing circuit;
   wherein the heating the substrate comprising passing a first current through a heater pattern affixed to the substrate;
   wherein the sensing circuit comprises:
      a first electrode affixed to the substrate and having a first plurality of fingers forming a first comb;
      a second electrode affixed to the substrate and having a second plurality of fingers forming a second comb, the second electrode disposed in spaced relation to the first electrode such that the first and second combs face each other;
      a semiconducting layer disposed over the first and second electrodes so as form a physical semiconductor bridge between the first and second electrodes;
   wherein passing the current through the sensing circuit comprises passing the current from the first electrode to the second electrode via the semiconducting layer;
   wherein the microchip oxygen sensor is disposed in an exhaust gas stream during the heating, the passing current, and the measuring;
   wherein the microchip oxygen sensor comprises the heater pattern, the first and second electrodes, and the semiconducting layer;
   wherein the microchip oxygen sensor further comprises a porous dielectric protective layer covering the semiconducting layer, wherein the porous dielectric protective layer contains a catalytic precious metal;
   wherein the substrate, electrodes, semiconducting layer, and protective layer are disposed in stacked order such that:
      the first and second electrodes are in direct contact with the semiconducting layer;
      the semiconducting layer is physically isolated from the substrate by electrodes;
      the protective layer is physically isolated from the combs of the electrodes by the semiconducting layer;
   wherein the method further comprises passing some of the exhaust gas through the protective layer to reach the electrodes.

2. The method of claim 1:
   wherein the semiconducting layer comprises a p-type semiconducting material;
   further comprising performing at least one of following in response to detecting rich exhaust gases based on a resistance of the microchip oxygen sensor:
      generating an alarm;
      disabling the combustion process.

3. The method of claim 1, wherein the semiconductor layer comprises an n-type semiconducting material.

4. The method of claim 1, wherein the combustion process occurs in a combustion chamber of an engine, and wherein the microchip oxygen sensor is exposed to exhaust gases from the engine.

5. The method of claim 4, wherein the engine is a multi-cylinder engine.

6. The method of claim 4, wherein the measuring the resistance of the oxygen sensing circuit comprises applying a voltage to the oxygen sensor via a voltage divider circuit contained in a wire harness connector operatively disposed between the microchip oxygen sensor and an electronic control unit of the engine.

7. The method of claim 6, wherein the measuring the resistance of the oxygen sensing circuit comprises applying a voltage to the microchip oxygen sensor via a voltage divider circuit contained in an electronic control unit of the engine.

8. The method of claim 1, wherein the semiconductor layer comprises an p-type semiconducting material.

\* \* \* \* \*